United States Patent [19]

Hohnjec et al.

[11] 4,183,865
[45] Jan. 15, 1980

[54] PROCESS FOR THE RESOLUTION OF RACEMIC α-AMINONITRILES

[75] Inventors: Marijan Hohnjec, Zagreb; Miha Japelj, Novo Mesto, both of Yugoslavia

[73] Assignee: KRKA, farmacevtika, kemija, kozmetika, zdravilisca in gostinstvo, Novo mesto, n.sol.o., Novo Mesto, Yugoslavia

[21] Appl. No.: 891,974

[22] Filed: Mar. 30, 1978

[30] Foreign Application Priority Data

Apr. 8, 1977 [YU] Yugoslavia ............................ 938/77

[51] Int. Cl.² ............................................. C07C 121/66
[52] U.S. Cl. ............................ 260/465 E; 260/465 D
[58] Field of Search ........................ 260/465 E, 465 D

[56] References Cited

U.S. PATENT DOCUMENTS

| | | |
|---|---|---|
| 3,344,023 | 9/1967 | Reinhold et al. ............ 260/465 E X |
| 3,480,670 | 11/1969 | Reinhold et al. ............ 260/465 E X |
| 3,658,876 | 4/1972 | Reinhold et al. ............ 260/465 E X |
| 3,715,382 | 2/1973 | Karaday et al. ............. 260/465 E X |
| 3,718,674 | 2/1973 | Karaday et al. ............. 260/465 E X |
| 3,723,496 | 3/1973 | Reinhold et al. ................ 260/465 E |

OTHER PUBLICATIONS

Stein et al., J.A.C.S., 77 (1955), pp. 700–703.

Primary Examiner—Joseph Paul Brust
Attorney, Agent, or Firm—Pollock, Vande Sande & Priddy

[57] ABSTRACT

Process for the resolution of certain racemic α-aminonitriles into optically active enantiomers which includes treating the racemic α-aminonitriles with (−)-dibenzoyl-tartaric acid in polar solvents to obtain a racemic mixture of diastereoisomeric D and L salts of (−)-dibenzoyl-tartaric acid, macerating the salts with dioxane, neutralizing the L-form, extracting the neutralized product, and converting it into a stable form.

17 Claims, No Drawings

PROCESS FOR THE RESOLUTION OF RACEMIC α-AMINONITRILES

The present invention relates to a process for the resolution of racemic alpha-aminonitriles of the general formula

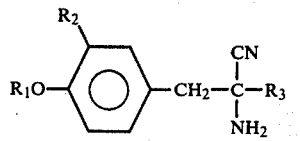

wherein
- $R_1$ stands for a hydrogen atom or a methyl group,
- $R_2$ stands for a hydrogen atom or a methoxy group, and
- $R_3$ stands for a hydrogen atom or a methyl group, into optically active enantiomers.

The resolution of racemic alpha-aminonitriles into the corresponding optically active enantiomers is the most important and economical step in the synthesis of optically active alpha-amino acids, especially in the synthesis of p-hydroxy-phenyl glycine, 3,4-dihydroxy-phenyl glycine, 3,4-dihydroxy-phenyl alanine (DOPA) and alpha-methyl-3,4-dihydroxy-phenyl alanine (methyl DOPA), which are important intermediates in pharmaceutical chemistry (Synthesis of methyl DOPA: G. Stein, H. A. Bronner and K. Pfister, J.Am.Chem.-Soc. 77, 700 (1955); antihypertensive activity of methyl DOPA: A. Sjoerdsma and S. Udenfriend, Biochem. Pharmacol. 8, 164 (1961)).

In the manufacture of optically active alpha-amino acids, the process comprising a preliminary resolution of the corresponding racemic alpha-aminonitriles and further chemical conversions of the isolated diastereoisomeric salts into the corresponding optically active alpha-amino acids offers a distinct economical and technological advantage over the process, wherein there is performed the resolution of the racemic alpha-amino acids into the corresponding optically active alpha-amino acids, especially as the other (inactive) diastereoisomer of the corresponding alpha-aminonitrile may be economically utilized and by means of racemization in alkaline media again converted into the corresponding D,L-aminonitrile. The racemization of the undesired optically active enantiomer of the corresponding alpha-amino acid is not feasible, which means that such a process offers substantially lower yields in the whole synthesis and is technologically inferior in comparison to the process based on preliminary resolution of the racemic aminonitriles. It has now been found that in accordance with the present inventive process the racemic alpha-aminonitriles may be resolved in a technologically advantageous manner into the corresponding optically active enantiomers as follows: Alpha-aminonitriles are treated with (−)-dibenzoyl-tartaric acid in suitable polar solvents like alkanols or ketones in order to obtain a racemic mixture of diastereoisomeric D and L salts of (−)-bibenzoyl-tartaric acid, which is macerated with aqueous dioxane (85 to 100% by volume) to yield L- and D-aminonitrile-(−)-dibenzoyl-bitartrate, the L-form is neutralized and the obtained product is extracted with a suitable chlorinated aliphatic hydrocarbon, whereupon it is converted into a stable form like a hydrochloride or an acyl derivative. The D-aminonitrile-(−)-dibenzoyl-bitartrate is racemized by means of ammonia and recycled.

The resolution of racemic D,L-aminonitriles by means of the optically active reactant (−)-dibenzoyl-tartaric acid is performed e.g. in methanol, ethanol, isopropanol or acetone. As a whole, the resolution of racemic aminonitriles in organic solvents represents a technological advantage over the resolution of D,L-aminonitriles by means of other optically active reactants in aqueous media, especially as said organic solvents may be regenerated in a simple manner. Likewise, the (−)-dibenzoyl-tartaric acid may be regenerated very simply and in a 90% yield. In the reaction of racemic D,L-aminonitriles of the general formula I with (−)-benzoyl-tartaric acid, first a racemic mixture of the corresponding diastereoisomeric D- and L-salts of (−)-benzoyl-tartaric acid is precipitated. The reaction is performed in organic solvents, preferably in methanol, and at ambient temperature.

The maceration of the obtained precipitated racemic salts by means of 85 to 100%, preferably 99% (by volume), aqueous dioxane causes the dissolving of the corresponding diastereoisomeric salt of (−)-dibenzoyl tartaric acid with D-aminonitrile, whereas the diastereoisomeric salt of (−)-dibenzoyl-tartaric acid with L-aminonitrile remains in the crystalline form. The neutralization of L-aminonitrile-(−)-dibenzoyl-bitartrate by means of ammonia, followed by an extraction with chloroform and a final precipitation with hydrochloric acid, yields the corresponding L-(+)-aminonitrile.hydrochloride. monohydrates of the general formula

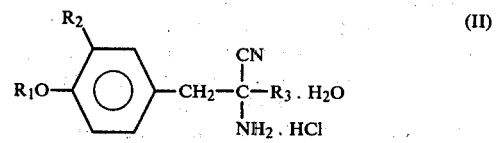

wherein $R_1$, $R_2$, $R_3$ have the meanings as defined in the general formula I.

L-aminonitrile may also be isolated in the form of more stable L-acyl-aminonitriles of the general formula

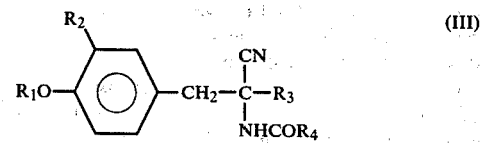

wherein $R_1$, $R_2$, $R_3$ have the meanings as defined in the general formula I, whereas $R_4$ stands for an alkyl group comprising 1 to 5 carbon atoms. L-acyl-aminonitriles are obtained by the reactions of the corresponding L-aminonitriles with acid anhydrides, preferably with acetic anhydride, in chlorinated aliphatic hydrocarbons, preferably in chloroform.

The (−)-dibenzoyl-tartaric acid is regenerated by means of acidification of an aqueous solution of ammonium dibenzoyl-tartrate.

The D-aminonitrile salt dissolved in dioxane is racemized with ammonia, followed by the isolation of D,L-aminonitrile and the regeneration of the second part of (−)-dibenzoyl-tartaric acid from the liquor, D,L-aminonitrile is recycled.

The hydrolysis of the corresponding L-aminonitrile.-hydrochloride.monohydrate or of L-acetylamino-nitrile may yield the L-form of amino acids.

The inventive process is illustrated more in detail, yet in no way limited by the following Examples.

EXAMPLE 1

17.6 g. (0.08 moles) of D,L-alpha-amino-(3,4-dimethoxy-benzyl)-propionitrile (D,L-aminonitrile) are dissolved in 90 ml. of ethanol and, at a temperature of 20° to 25° C., there are added 30 g. (0.083 moles) of (−)-dibenzoyl-tartaric acid, dissolved in 40 ml. of ethanol. The reaction solution is stirred and cooled down to 0° to 5° C. and kept stirring for 2 hours at this temperature. The obtained precipitate is filtered, washed with two 10 ml.-portions of cooled ethanol and dried. There are obtained 41.6 g. (90%) of a mixture of diastereoisomeric salts, m.p. of 170° to 176° C. and $/\alpha/_D{}^{25} = -76.25°$ (c=2, methanol). The obtained salt is suspended in 198 ml. of dioxane and 2 ml. of water and vigorously stirred for 48 hours at 22° C. The precipitate is filtered off, whereupon it is dried. There are obtained 19 g. (41%) of L-aminonitrile-dibenzoyl-bitartrate, $/\alpha/_D{}^{20} = -89.7°$ (c=2, methanol). The thus obtained precipitate is suspended in 200 ml. of water, cooled down to 0° to 3° C., thereupon there are added 30 ml. of chloroform and the pH is adjusted to 6.9 by means of 6 N ammonia. The layers are separated and the aqueous layer is extracted with two 5 ml.-portions of chloroform. To the aqueous layer there is added 4 N HCl until a pH of 3.5 is reached, whereupon the separating monohydrate of (−)-dibenzoyl-tartaric acid is filtered off, washed with water and dried. There is obtained the pure (−)-dibenzoyl-tartaric acid (13.8 g.; 44%), having a m.p. of 89° to 90° C. and $/\alpha/_D{}^{25} = -117.5°$ (c=4, ethanol). The combined chloroform extracts are added dropwise to 30 ml. of cooled 6 N hydrochloric acid (0° to 5° C.). The reaction suspension is kept stirring for 2 hours at this temperature and filtered. The precipitate is washed with 10.1 of cooled chloroform and dried. There are obtained 8.6 g. (39%) of L-(+)-aminonitrile·hydrochloride·monohydrate, $/\alpha/_D{}^{20} = +9.8°$ (c=2, methanol).

The dioxane solution of D-aminonitrile-dibenzoyl-bitartrate is evaporated under reduced pressure (50 mm Hg) in to a thick oil, whereupon 20 ml. of a 2 N ammonia solution are added to the residue and it is heated for 30 minutes to 50° C. The suspension is cooled down to 0° C., stirred at this temperature for 2 hours, the precipitate is filtered off and washed with two 10 ml.-portions of water. There are obtained 7.92 g. (45%) of D,L-aminonitrile with a m.p. of 83° to 85° C. The liquor is partially evaporated under reduced pressure (50 mm Hg) and acidified with 4 N HCl until a pH of 3.5 is reached. The separating monohydrate of (−)-dibenzoyl-tartaric acid is filtered off and washed with water. There are obtained 14.5 g. (46%) of (−)-dibenzoyl-tartaric acid, m.p. of 88° to 90° C. and $/\alpha/_D{}^{25} = -116.0°$ (c=4, ethanol). There are regenerated totally 28.3 g. (90%) of (−)-dibenzoyl-tartaric acid.

EXAMPLE 2

41.6 g. of a mixture of diastereoisomeric salts, obtained in accordance with the process of Example 1, are macerated and the L-form is extracted by means of chloroform, as in Example 1. 10 ml. of acetanhydride are added to the chloroform solution and the chloroform is distilled off. The reaction solution is heated for 5 minutes at 100° C., whereupon, during 30 minutes, it is cooled down to 10° C. 10 ml. of isopropanol are added and the crystals of L-acetyl-aminonitrile are filtered off and washed with 10 ml. of isopropanol. There are obtained 7.8 g. (37%) of L-acetyl-aminonitrile, m.p. 137° to 141° C. and $/\alpha/_D{}^{20} = -29.5°$ (c=2, methanol).

What is claimed is:

1. Process for the resolution of racemic α-aminonitriles of the general formula:

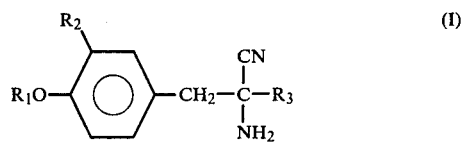

wherein
R₁ stands for a hydrogen atom or a methyl group,
R₂ stands for a hydrogen atom or a methoxy group, and
R₃ stands for a hydrogen atom or a methyl group,
into optically active enantiomers, which comprises:
(A) treating said racemic α-aminonitriles with (−)-dibenzoyl-tartaric acid in organic polar solvent in order to thereby obtain a macemic mixture of diastereoisomeric D and L salts of (−)-dibenzoyl-tartaric acid;
(B) macerating said racemic mixture of diastereoisomeric D and L salts of (−)-dibenzoyl-tartaric acid with dioxane or water/dioxane mixture containing at least 85% by volume dioxane to thereby obtain D- and L-aminonitrile (−)-dibenzoyl-bitartrate;
(C) neutralizing the L-form;
(D) extracting the neutralized product obtained in step (C) above with a chlorinated aliphatic hydrocarbon; and
(E) converting said neutralized product to a hydrochloride or acetyl derivative.

2. Process as claimed in claim 1, characterized in that D-aminonitrile-(−)-dibenzoyl-bitartrate is racemized by means of ammonia and recycled.

3. The process of claim 1 wherein said polar solvent is selected from the group of alkanol, and acetone.

4. The process of claim 3 wherein said alkanol is selected from the group of methanol, ethanol, and isopropanol.

5. The process of claim 1 wherein said L-form is neutralized with ammonia.

6. The process of claim 1 wherein said chlorinated aliphatic hydrocarbon is chloroform.

7. The process of claim 1 wherein the macerization is performed at a temperature of 22° C.

8. The process of claim 7 wherein the treating with (−)-dibenzoyl-tartaric acid is performed at a temperature of about 0°–5° C.

9. The process of claim 1 wherein the treating with (−)-dibenzoyl-tartaric acid is performed at a temperature of about 0°–5° C.

10. The process of claim 1 wherein said water/dioxane mixture contains about 99% by volume of dioxane.

11. The process of claim 1 wherein said polar solvent is selected from the group of methanol, isopropanol, and acetone, said chlorinated aliphatic hydrocarbon is chloroform; the treating with (−)-dibenzoyl-tartaric acid is performed at about 0° to 5° C.; and the macerization is performed at a temperature of 22° C.

12. The process of claim 11 wherein said L-form is neutralized with ammonia.

13. The process of claim 1 wherein the racemic α-aminonitrile is D,L-amino-(3,4-dimethoxy-benzyl)-propionitrile.

14. The process of claim 1 wherein the salt of D-aminonitrile with (−)-mandelic acid is racemized in alkaline media into the corresponding D,L-aminonitrile and recycled to the process.

15. The process of claim 11 wherein the salt of D-aminonitrile with (−)-mandelic acid is racemized in alkaline media into the corresponding D,L-aminonitrile and recycled to the process.

16. The process of claim 1 wherein said organic polar solvent includes a ketone.

17. The process of claim 1 wherein said organic polar solvent includes an alkanol.

* * * * *